(12) United States Patent
Suzuki et al.

(10) Patent No.: US 10,166,152 B2
(45) Date of Patent: Jan. 1, 2019

(54) ABSORBENT ARTICLE

(71) Applicant: DAIO PAPER CORPORATION, Shikokuchuo-shi, Ehime (JP)

(72) Inventors: Yoko Suzuki, Sakura (JP); Kaori Umemoto, Sakura (JP)

(73) Assignee: DAIO Paper Corporation, Ehime (JP)

( * ) Notice: Subject to any disclaimer, the term of this patent is extended or adjusted under 35 U.S.C. 154(b) by 335 days.

(21) Appl. No.: 14/916,457

(22) PCT Filed: Sep. 4, 2014

(86) PCT No.: PCT/JP2014/073315
§ 371 (c)(1),
(2) Date: Mar. 3, 2016

(87) PCT Pub. No.: WO2015/033995
PCT Pub. Date: Mar. 12, 2015

(65) Prior Publication Data
US 2016/0213525 A1 Jul. 28, 2016

(30) Foreign Application Priority Data

Sep. 4, 2013 (JP) ................................. 2013-182857

(51) Int. Cl.
*A61F 13/15* (2006.01)
*A61F 13/475* (2006.01)
*A61F 13/511* (2006.01)
*A61F 13/56* (2006.01)

(52) U.S. Cl.
CPC ...... *A61F 13/4758* (2013.01); *A61F 13/4756* (2013.01); *A61F 13/51108* (2013.01); *A61F 13/5611* (2013.01)

(58) Field of Classification Search
CPC .............. A61F 13/4758; A61F 13/4756; A61F 13/51108; A61F 13/5611
USPC ............................ 604/378, 379, 380, 385.01
See application file for complete search history.

(56) References Cited

U.S. PATENT DOCUMENTS 6,099,515 A  8/2000  Sugito

FOREIGN PATENT DOCUMENTS

| JP | 10-234775 | 9/1998 |
|---|---|---|
| JP | 11-216161 | 8/1999 |
| JP | 3406214 | 3/2003 |
| JP | 2007-117727 | 5/2007 |
| JP | 2010-246896 | 11/2010 |
| JP | 4683892 | 2/2011 |
| JP | 2012-5539 | 1/2012 |
| JP | 5105884 | 10/2012 |
| JP | 5132264 | 11/2012 |

*Primary Examiner* — Jacqueline Stephens
(74) *Attorney, Agent, or Firm* — Norris McLaughlin, P.A.

(57) ABSTRACT

In an incontinence pad having an absorber 4 interposed between a permeable front surface sheet and a back surface sheet, the absorber is provided with an absorber recessed part, without relying on compression, on a surface of the permeable front surface sheet along an incontinence pad longitudinal direction and over a longitudinal direction range including a body fluid discharge site. By embossing from a front surface of the permeable front surface sheet, an embossed part imparted with an emboss width smaller than a groove width of the absorber recessed part is disposed along the absorber recessed part in the inside of the absorber recessed part.

4 Claims, 10 Drawing Sheets

ABSORBENT ARTICLE

BACKGROUND OF THE INVENTION

The present invention relates to an absorbent article mainly used in incontinence pads, sanitary napkins, vaginal discharge sheets, medical pads, toiletry goods, and disposable diapers, and particularly relates to an absorbent article in which a recessed groove is formed along a longitudinal direction on a from surface.

Absorbent articles having an absorber interposed between an impermeable back surface sheet such as a polyethylene sheet or a polyethylene sheet laminated nonwoven fabric and a permeable front surface sheet such as a nonwoven fabric or a permeable plastic sheet have been known.

Various improvements have also been added to this kind of absorbent article and various kinds of absorbent articles provided with a recessed groove along a longitudinal direction on a front surface have been proposed. For example, disclosed in the following Japanese Patent No. 5132264 is an absorbent article in which a high-center part located substantially in a center part of a lower layer absorber has a dent formed substantially at a center on a skin-contact surface and extending in a longitudinal direction, and a part that forms the dent of the high-center pan has a protruded pan of a lower surface of die upper layer absorber protruded toward a non-skin-contact surface and a recessed part of an upper surface of the lower layer absorber that contacts with the protruded pan and forms one body therewith, a bottom part of the dent sinks on the lower layer absorber, and both the upper layer absorber and the lower layer absorber include an absorbent fibrous material consolidated in the periphery of an uneven sunken part.

Further, in the following Japanese Patent No. 510884, an absorbent article in which a recessed part extending in a longitudinal direction of the absorbent article is integrally formed on a front surface sheet and an absorption layer is disclosed.

In Japanese Patent No. 3406214, a disposable diaper in which, between side surfaces that are formed by dividing a core and that face each other, a front surface sheet hangs down along the side surface to come into contact with a back surface sheet, and at the contact site, the front and back surface sheets are joined with each other is disclosed.

In Japanese Unexamined Patent Application No. 2007-117727A, an absorbent article in which a superabsorbent polymer is mixed in the inside of an absorber, and a part or an entirety of the superabsorbent polymer is eccentrically disposed on a peripheral wall and/or a bottom surface part of a feces pocket is disclosed.

In Japanese Patent No. 4683892, an absorbent pad is disclosed, wherein in the absorbent pad a first flexible shaft extending along a vertical axis, and a pair of second and third flexible shafts that separate to both sides in a direction of a horizontal axis from the first flexible shaft and extend in a direction of the vertical axis are located, the first flexible shaft is a penetration gutter formed by absence of an absorbent fiber between a surface that absorbs a body fluid and a surface on an opposite side, and the second and third flexible shafts are strip grooves formed by a part in which a thickness of the absorbent fiber is thinner than another part.

SUMMARY OF THE INVENTION

However, in the absorbent article described in Japanese Patent No. 5132264, both the upper layer absorber and the lower layer absorber have a consolidated absorbent fibrous material in the periphery of the uneven sunken part. Therefore, when the consolidated absorbent fibrous material expands due to a body fluid that has permeated into the absorber from the dent of the high-center part the dent becomes shallow, and an effect of providing the dent may be largely degraded. Further, also in the absorbent article described in Japanese Patent No. 5105884, when body fluid permeates into the recessed part formed by compression and a polymer or a pulp in the surroundings of the recessed part absorbs liquid and swells, absorptivity of the body fluid deteriorates because the bottom surface of the recessed part swells up and both side surfaces jut into the recessed part to clog the recessed part. Further, like in Japanese Patent No. 5132264 and Japanese Patent No. 5105884, when the recessed part is formed by compressing the absorber, the absorber is consolidated by compression and is hardened by thermal compression bonding, thereby creating discomfort for the wearer.

Further, in the disposable diaper described in Japanese Patent No. 3406214, when the polymer or the like expands during water absorption, a side surface bulges in the slit of the absorber. However, this expansion cannot be effectively suppressed because a front surface sheet is disposed along an internal surface of the slit. Therefore, due to the bulging of the side surface, a slit width of the absorber becomes smaller and the volume of receivable body fluid is reduced. Likewise, in Japanese Unexamined Patent Application Publication No. 2007-117727A, there is a concern that the volume of the feces pocket is reduced due to the expansion when the superabsorbent polymer absorbs water and a volume of receivable excrement decreases because the superabsorbent polymer is eccentrically disposed in the surroundings of the feces pocket formed by the recessed part of the absorber.

Further, in the absorbent pad described in Japanese Patent No. 4683892, the first flexible shaft is formed by the penetration gutter. However, there was a problem that a hollow state of the penetration gutter is difficult to maintain because the front surface sheet and the back surface sheet are disposed so as to cover a front surface and a back surface of the penetration gutter. That is, there is a concern that body fluid may not be received due to the penetration gutter collapsing by the application of only a slight external force such as body pressure.

Moreover, users of incontinence pads in particular vary greatly depending on individual symptoms; some people have a small urination amount but urinate frequently, and others discharge a lot at one time. For persons who urinate frequently, it is cumbersome to change an incontinence pad at the time of every urination. Therefore, an incontinence pad in which absorption performance does not degrade after one urination and that maintains its initial absorption performance has been demanded. Further, for persons who discharge a lot at one time, often a conventional incontinence pad cannot give satisfaction because it has a slow absorption rate. Therefore, speedily absorbing a lot of urine discharged at one time has also been a required function of incontinence pads.

SUMMARY OF THE INVENTION

Therefore, a primary object of the present invention is to provide, in an absorbent article in which a recessed groove is formed along a longitudinal direction on a front surface, an absorbent article that maintains an effect of the recessed groove, does not decrease in absorption rate, and prevents wear feeling from deteriorating, even during water absorption or when an external force is applied.

As a first aspect of the present invention for solving the above problem, in an absorbent article having an absorber interposed between a permeable front surface sheet and a back surface sheet, the absorber includes an absorber recessed part formed into a recessed groove shape or into a slit shape, without relying on compression, on a surface of the permeable front surface sheet along an absorbent article longitudinal direction and over a longitudinal direction range including a body fluid discharge site, and by embossing from a front surface of the permeable front surface sheet, an embossed part imparted with an emboss width smaller than a groove width of the absorber recessed part is disposed along the absorber recessed part in the inside of the absorber recessed part.

According to the first aspect of the invention, the absorber recessed part is formed in the absorber without relying on compression, and the embossed part is disposed to the absorber recessed part by embossing from a front surface of the permeable front surface sheet. Here, when a case where body fluid enters the absorber recessed part and the polymer or pulp surrounding the absorber recessed part expands is considered, in the case where the absorber recessed part is formed into a recessed groove shape, embossing on a bottom surface of the absorber recessed part is suppressed to be very small in comparison with a bottom surface in which the polymer or pulp is made high in density by compression. Further, a side surface of the absorber recessed part is also suppressed to be small in terms of expansion of both side surfaces because the permeable front surface sheet is interposed in the absorber recessed part due to the embossing part. Therefore, the absorption property of body fluid can be prevented from deteriorating due to clogging of the absorber recessed part by the polymer or pulp expanded during liquid absorption. On the other hand, in the case where the absorber recessed part is formed into a slit shape, the bottom surface does not expand because the absorber is not interposed on the bottom surface of the absorber recessed part. Further, both side surfaces are suppressed from expanding by the permeable front surface sheet in the same manner as above. In the above explanation, a "groove" does not extend all the way through the depth of absorber whereas a "slit" does extend all the way through. However, in the claims, to avoid prolixity, the term "groove" is intended to be inclusive also of a slit if not limited to a slit by additional structural recitations.

Furthermore, a gap is disposed between the permeable front surface sheet interposed in the absorber recessed part by the embossed part and a side surface of the absorber recessed part because an emboss width A of the embossed part is formed smaller than a groove width B of the absorber recessed part. This gap works as a buffer zone in which body fluid passed through the permeable front surface sheet during permeation of the body fluid is temporarily stored and also works as a buffer region when the absorber absorbs the body fluid and a side surface of the absorber recessed pan expands. Therefore, even when a large amount of body fluid is discharged at once, the body fluid can be rapidly absorbed, the absorption rate can be expedited, and the absorber recessed pan is prevented from being clogged by one discharge. Therefore, even when urination is repeated many times, initial absorption performance can be maintained.

Further, there is neither consolidation due to compression of the absorber nor hardening due to heating and melting; the flexibility of the absorber can be maintained; and excellent wearability can be maintained because the absorber recessed part is formed not by compression, but by fiber-stacking or by a laminate structure of the absorber, for example, for an article having a recessed groove shape.

Since the embossed part is disposed in the inside of the absorber recessed part by embossing from a front surface of the permeable front surface sheet, the permeable front surface sheet is interposed in the absorber recessed part. Therefore, a structure in which the absorber recessed part for receiving body fluid hardly collapses and can rapidly absorb body fluid even when an external force is applied can be maintained.

As a second aspect of the invention, the absorbent article according to the first aspect having a ratio of an emboss width A of the embossed part and a groove width B of the absorber recessed part, A/B, of 0.5 or more and less than 1 is provided.

In the second aspect of the invention, by defining the ratio of the emboss width A of the embossed part and the groove width B of the absorber recessed part, A/B, in a defined range, shape retention of the absorber recessed part is made excellent, and a function of receiving body fluid is further maintained.

As a third aspect of the invention, the absorbent article according to the first or second aspect in which a second sheet is disposed between the permeable front surface sheet and the absorber, and the embossed part (i.e., embossment) is imparted to a laminated body of the permeable front surface sheet and the second sheet is provided.

In a third aspect of the invention, when the second sheet is disposed between the permeable front surface sheet and the absorber, the embossed part is imparted to the front surface sheet together with the second sheet.

As a fourth aspect of the invention, the absorbent article according to any one of the first to third aspects in which one embossed part is disposed at a center in a width direction in the absorber recessed part or a plurality of embossed parts are disposed one by one on each of both sides in the absorber recessed part is provided.

The fourth aspect of the invention defines an arrangement aspect of the embossed part imparted to the inside of the absorber recessed part. One embossed part can be disposed at a center in a width direction in the absorber recessed part or embossed pans can be disposed one by one on each of both sides in the absorber recessed part.

As a fifth aspect of the invention, the absorbent article according to any one of the first to fourth aspects of the invention in which only one section of the absorber recessed part is formed at a center in the width direction of the absorbent article or a plurality of sections is formed along a longitudinal direction and spaced in the width direction is provided.

In the fifth aspect of the invention, an arrangement aspect of the absorber recessed part formed in the absorber is defined. The absorber recessed part can be formed with only one section at a center in the width direction of the absorbent article or with a plurality of sections along a longitudinal direction and spaced in the width direction.

As a sixth aspect of the invention, the absorbent article according to any one of the first to fifth aspects in which a back-end of the absorber recessed part extends to a back side past a buttocks start position on a crotch side of a wearer is provided.

In the sixth aspect of the invention, as will be detailed below, in order to prevent lateral leakage of body fluid that flows through the absorber recessed part by wrinkles generated when the absorbent article is curved along roundness of the hip, a back-end of the absorber recessed part is disposed so as to extend to a back side past the buttocks start position on a crotch side of the wearer.

As a seventh aspect of invention, the absorbent article according to any one of the first to sixth aspects in which a slippage prevention adhesive layer is disposed on an external surface of the back surface sheet, and the slippage prevention adhesive layer is not disposed in a region that overlaps with the absorber recessed part is provided.

In the seventh aspect of the invention, if the slippage prevention adhesive layer would be disposed in a region that overlaps with the absorber recessed part that has a thin absorber thickness and deforms easily, there is a concern that as underwear moves, the absorber recessed part is likely to be deformed. Therefore, the slippage prevention adhesive layer is not disposed in a region that overlaps with the absorber recessed part so as not to be influenced by movement of the underwear; moreover, if adhesive layers would be disposed in this region, the adhesive layers may adhere with each other.

As was described above, the present invention provides an absorbent article in which a recessed groove is formed along a longitudinal direction on a from surface; when an external force is applied during liquid absorption, an effect of the recessed groove can be maintained; absorption rate does not decrease; and wearability is maintained.

BRIEF DESCRIPTION OF THE DRAWINGS

FIGS. 9(A) and 9(C) show a comparative example and FIGS. 9(B) and 9(D) show the present invention, wherein FIGS. 9(A) and 9(B) show cross sectional views of a wearing state, and FIGS. 9(C) and 9(D) show a plan view of the incontinence pad 1 that shows generation of wrinkles in the wearing state.

Hereinafter, an embodiment of the present invention will be described with reference to the drawings.

[Fundamental Configuration of Incontinence Pad 1]

An incontinence pad 1 according to the present invention mainly includes, as shown in FIGS. 1, 1(A), 2 and 3 an impermeable back surface sheet 2 made of a polyethylene sheet or the like; a permeable front surface sheet 3 into which urine or the like smoothly permeates; an absorber 4 made of a cotton-like pulp or synthetic pulp interposed between these sheets 2, 3; a hydrophilic second sheet 6 disposed as needed between the permeable front surface sheet 3 and the absorber 4; and side nonwoven fabrics 7, 7 that form a pair of right and left solid gathers BS, BS disposed with a rough edge part of the absorber 4 as a standing base end and protruding to a skin side within a predetermined interval in a longitudinal direction so as to contain at least a body fluid discharge site. In the surroundings of the absorber 4, in an end edge part in a longitudinal direction, external edge parts of the impermeable back surface sheet 2 and the permeable front surface sheet 3 are bonded by an adhesive such as a hot melt or an adhesion means such as heat sealing. Further, at both side edge parts, the impermeable back surface sheet 2 and the side nonwoven fabrics 7 which extend more sideward than the absorber 4 are bonded by an adhesive such as a hot melt or an adhesion means such as heat sealing. The absorber 4 can be surrounded by a covering sheet such as a crepe paper or a nonwoven fabric (not shown) to improve shape retention and diffusion property.

Hereinafter, a structure of the incontinence pad 1 will be described in more detail. As the impermeable back surface sheet 2, while a sheet material having at least water shieldability such as polyethylene or polypropylene is used, other than these, a sheet of nonwoven fabric that substantially secures impermeability by interposing a water-proof film (in this case, the water-proof film and the nonwoven fabric constitute the impermeable back surface sheet) or the like can be used. Recently, from the viewpoint of dampness prevention, a permeable substance is preferably used. As the water-shielding and permeable sheet material, a microporous sheet obtained by stretching in a uniaxial or biaxial direction after a sheet is molded by melt-kneading an inorganic filler in an olefinic resin such as polyethylene or polypropylene can be suitably used.

As the permeable front surface sheet 3, a porous or nonporous nonwoven fabric or a porous plastic sheet can be suitably used. Nonwoven fabrics obtained with, other than synthetic fibers such as olefin based fibers such as polyethylene or polypropylene, polyester based fibers, and polyamide based fibers, recycled fibers such as rayon and cupra, and natural fibers such as cotton as a raw material fiber that constitutes a nonwoven fabric, and according to an appropriate processing method such as a spun lace method, a spun bond method, a thermal bond method, a melt blown method, and a needle punch method can be used. Among these processing methods, the spun lace method is excellent in terms of the non woven fabric being excellent in flexibility and drape properly, and the thermal bond method is excellent in terms of the nonwoven fabric being bulky and soft.

The absorber 4 is formed of an absorbent fiber such as a fluff-like pulp and a superabsorbent polymer 8 and, in an illustrated example, a planar shape is formed into a vertically long substantially oval shape that is elongated in a pad longitudinal direction. The superabsorbent polymer 8 is formed into granular powder, for example, and is dispersed and mixed in the pulp to constitute the absorber 4. The absorber 4 includes the absorber recessed part 20 for body fluid inflow on a surface on the permeable front surface sheet 3, and this constitution will be described in more detail below.

As the pulp, a chemical pulp obtained from wood, and pulps made of cellulose fibers such as dissolving pulp and synthetic cellulose fibers such as rayon and acetate can be used. A softwood pulp having a fiber length longer than that of a hardwood pulp is suitably used from the viewpoint of function and price. Though not shown in the drawing, in the case where the absorber 4 is surrounded by a covering sheet, the covering sheet is eventually interposed between the permeable front surface sheet 3 and the absorber 4, whereby the covering sheet, having excellent absorption property, rapidly diffuses body fluid, and urine and the like can be prevented from rebounding.

As the superabsorbent polymer 8, for example, substances obtained by partially crosslinking water-swellable polymers such as a polyacrylic acid salt crosslinked product, a self-crosslinked polyacrylic acid salt, a saponified product of acrylic acid ester-vinyl acetate copolymer crosslinked product, an isobutylene/maleic anhydride copolymer crosslinked product, a polysulfonate crosslinked product, polyethylene oxide, and polyacryl amide can be used. Among these, acrylic acid—or acrylic acid salt-based products having an excellent water absorption amount and water absorption rate are suitable. A water absorption force (absorption ratio) and water absorption rate of the superabsorbent polymer having the above-described water absorption property can be adjusted by controlling a crosslinking density and a crosslinking density gradient in a manufacturing process.

Further, the absorber 4 may be mixed with a synthetic fiber. As the synthetic fiber, for example, polyolefin-based fibers such as polyethylene or polypropylene, polyester-based fibers such as polyethylene terephthalate or polybutylene terephthalate, polyamide-based fibers such as nylon, and copolymers thereof can be used, and mixtures of two kinds of these may be used. Further, a sheath/core type fiber having a fiber having a high melting point as a core and a fiber having a low melting point as a sheath, a side by side type fiber, and a composite fiber such as divided fiber can be also used. When the synthetic fiber is a hydrophobic fiber, it is desirable to use one that has been surface treated with a hydrophilizing agent to impart affinity to body fluid.

The above-described second sheet 6 may have a hydrophilic property whereby body fluid is drawn thereto. Specifically, by using recycled fiber such as rayon or cupra, or natural fiber such as cotton, fibers having a hydrophilic property in the raw material itself are used, or fibers to which a hydrophilic property is imparted by surface treating synthetic fibers such as olefin-based fibers such as polyethylene or polypropylene, polyester-based fibers, or polyamide-based fibers with a hydrophilizing agent can be used. Further, the second sheet 6 may have a porous film layer on a back surface (facing absorber 4) to give stiffness, or may be formed into a laminated sheet with a covering sheet, or a raw material containing pulp may be used.

On both side parts on a front surface of the incontinence pad 1, along a longitudinal direction and over an entire length of the incontinence pad 1, side nonwoven fabrics 7, 7 are disposed, and external parts of the side nonwoven fabrics 7, 7 are laterally extended. Further, the impermeable back surface sheet 2 is laterally extended, and these side nonwoven fabric 7 parts and the impermeable back surface sheet 2 part which are laterally extended, are joined with a hot-melt adhesive to form a side flap.

As the side nonwoven fabric 7, from an important function point of view, water-repellent finish nonwoven fabric or hydrophilized nonwoven fabric can be used. For example, when placing importance on a function such as prevention of inflow of urine, or improvement in a skin-contact feeling, water repellent finish nonwoven fabrics such as SSMS (spun-spun-melt-spun), SMS (spun-melt-spun) and SMMS (spun-spun-melt-spun) coated with a silicone-based, paraffin-based, or alkyl chromic chloride-based water repellent agent can be desirably used, and when placing importance on the absorption property of body fluid, it is desirable to use a hydrophilized nonwoven fabric to which hydrophilicity is imparted by making use of a capillary phenomenon after a synthetic fiber is swollen or made porous by using a method of making a synthetic (polymeric) fiber having a hydrophilic group, by copolymerizing for example an oxidation product of polyethylene glycol in the manufacturing process of the synthetic fiber, or a method of treating the synthetic fiber with a metal salt such as stannic chloride to make it porous by partially dissolving a surface and to deposit on it a hydroxide of metal. As such a side nonwoven fabric 7, a nonwoven fabric formed according to an appropriate processing method with a natural fiber, a synthetic fiber or a recycled fiber as a raw material can be used.

The side nonwoven fabrics 7, 7, by being appropriately folded up, constitute a solid gather BS having a 2-fold gather structure formed of a pair of left and right internal solid gathers 10, 10 standing on a skin side with a portion in the vicinity of the side edge of the absorber 4 as a standing base end, and a pair of left and right external solid gathers 11, 11 that are located relatively further outside than the internal solid gathers 10 and stand on a skin side formed by the impermeable back surface sheet 2 and the side nonwoven fabric 7 which extend more laterally than the absorber 4. It should be noted that the above-described solid gather BS may be a single-fold gather structure formed only of either the internal solid gather 10 or the external solid gather 11, or may not be formed in a solid gather shape standing on a skin side by only disposing the side nonwoven fabric 7.

Figure 2:
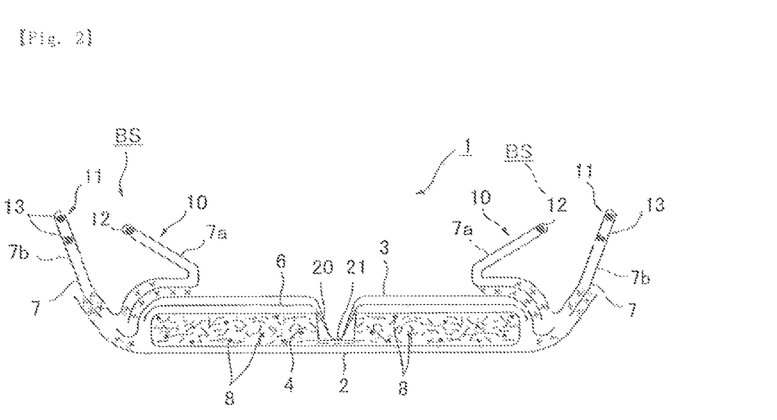
FIG. 2 is a cross-sectional view taken along a II-II line of FIG. 1.
Figure 3:
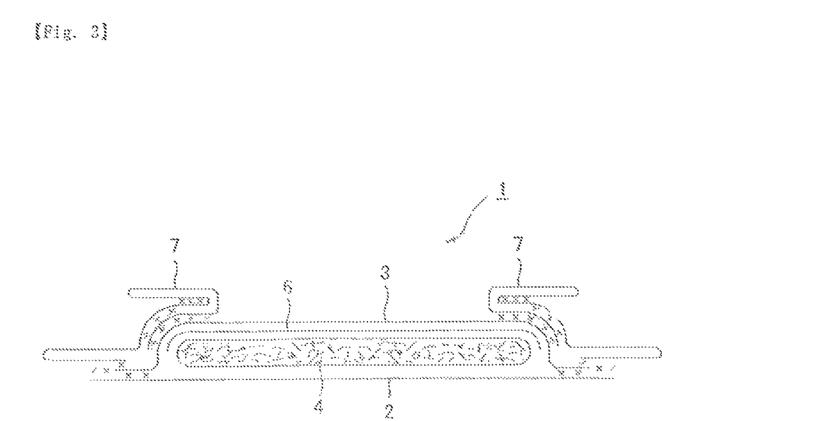
FIG. 3 is a cross-sectional view taken along a III-III line of FIG. 1.

Structures of the internal solid gather 10 and external solid gather 11 will be described in more detail. In the side nonwoven fabric 7, as shown in FIG. 2, both side edges thereof in a width direction are folded back to the pad back surface to form 2-fold sheet parts 7a, 7b, respectively, on the inside in a width direction and on the outside in a width direction. One or a plurality, one in the illustrated example, of a filamentous elastic member 12 which at both ends or at an appropriate point or segment thereof in a longitudinal direction is fixed to the inside of the 2-fold sheet parts 7a on the inside in the width direction is provided, and one or a plurality, two in the illustrated example, of filamentous elastic members 13, 13 which at both ends or an appropriate point or segment thereof in a longitudinal direction is fixed to the inside of the 2-fold sheet parts 7b on the outside in the width direction are provided. A base end part of the two-fold sheet part 7a on the inside in the width direction is adhered to a top surface of the permeable front surface sheet 3 disposed to a side part of the absorber 4 with a hot-melt adhesive, a base end part of the two-fold sheet part 7b on the outside in the width direction is adhered to a side end part of the impermeable back surface sheet 2 extended more laterally than the absorber 4 with a hot-melt adhesive, and thereby the internal solid gather 10 standing on a skin side by the two-fold sheet part 7a on the inside in the width direction is formed, and the external solid gather 11 standing on a skin side by the two-fold sheet part 7b on the outside in the width direction is formed. It should be noted that the side nonwoven fabric 7 is not provided with the filamentous elastic members 12, 13 at both end parts in a pad longitudinal direction as shown in FIG. 3, and the two-fold sheet part 7a on the inside in the width direction is joined to the absorber 4 side with a hot-melt adhesive or the like.

(Configuration of Recessed Groove)

In the present incontinence pad 1, a recessed groove for body fluid inflow is formed on a front surface along a longitudinal direction. The recessed groove receives the body fluid discharged on a front surface of the permeable front surface sheet 3, temporarily stores the body fluid, induces diffusion of the body fluid to a front-back direction, and resultantly expedites an absorption rate of the body fluid to the absorber 4 to prevent lateral leakage.

Figure 1:
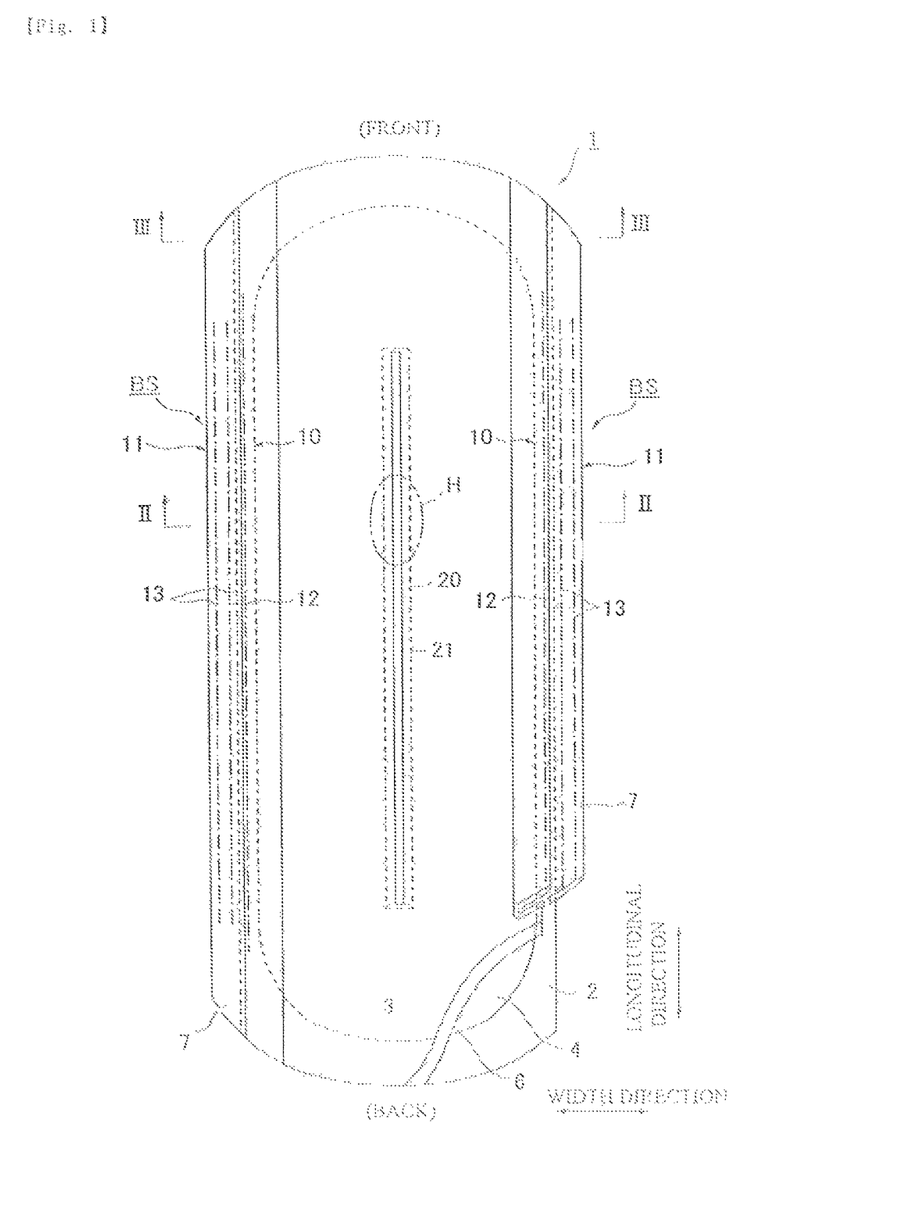
FIG. 1 is a partially broken development view of an incontinence pad according to the present invention.
Figure 4:
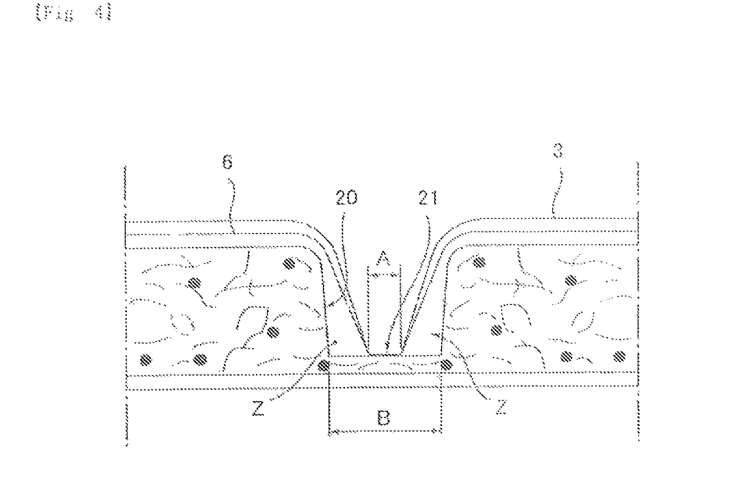
FIG. 4 is an expanded sectional view of the vicinity of an absorber recessed part 20.

A structure of the recessed groove will be described in more detail. As shown in FIG. 1 and FIG. 4, the absorber 4 includes the absorber recessed part 20 formed into a recessed groove shape or into a slit shape (into a recessed groove shape in the illustrated example) without relying on compression on a surface (surface on a skin side) of the permeable front surface sheet 3 along a pad longitudinal direction and over a longitudinal direction range including a body fluid discharge site H.

Figure 5A:
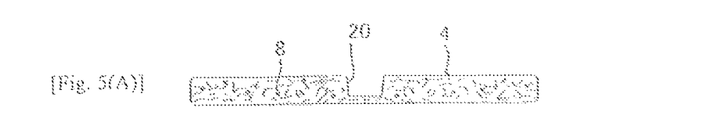
FIGS. 5(A) and 5(B) are sectional views of an absorber 4.
Figure 5B:
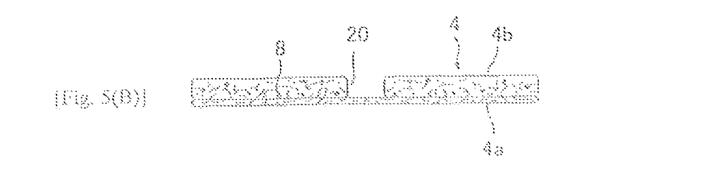

The absorber recessed part 20 is a non-penetration type recessed part having a bottom surface depressed to the impermeable back surface sheet 2 whereas the rest of the absorber extends upward toward front surface sheet 3, and is formed, without relying on compression, as shown in, for example, FIG. 5(A), by fiber stacking, or by in FIG. 5(B), a laminated structure of a lower layer absorber 4a preferably of a lesser thickness forming a bottom part of the absorber recessed part 20 and an upper layer absorber 4b preferably of a greater thickness in which the absorber recessed part 20 is formed.

Then, in the present incontinence pad 1, with the permeable front surface sheet 3 and, as needed, the second sheet 6 laminated on a skin side of the absorber 4, by embossing from a front surface (skin surface) of the permeable front surface sheet 3, an embossed part (embossment) 21 imparted with an emboss width A smaller than a groove width B of the absorber recessed part 20 is disposed along the absorber recessed part 20 in the inside of the absorber recessed part 20.

Figure 1A:
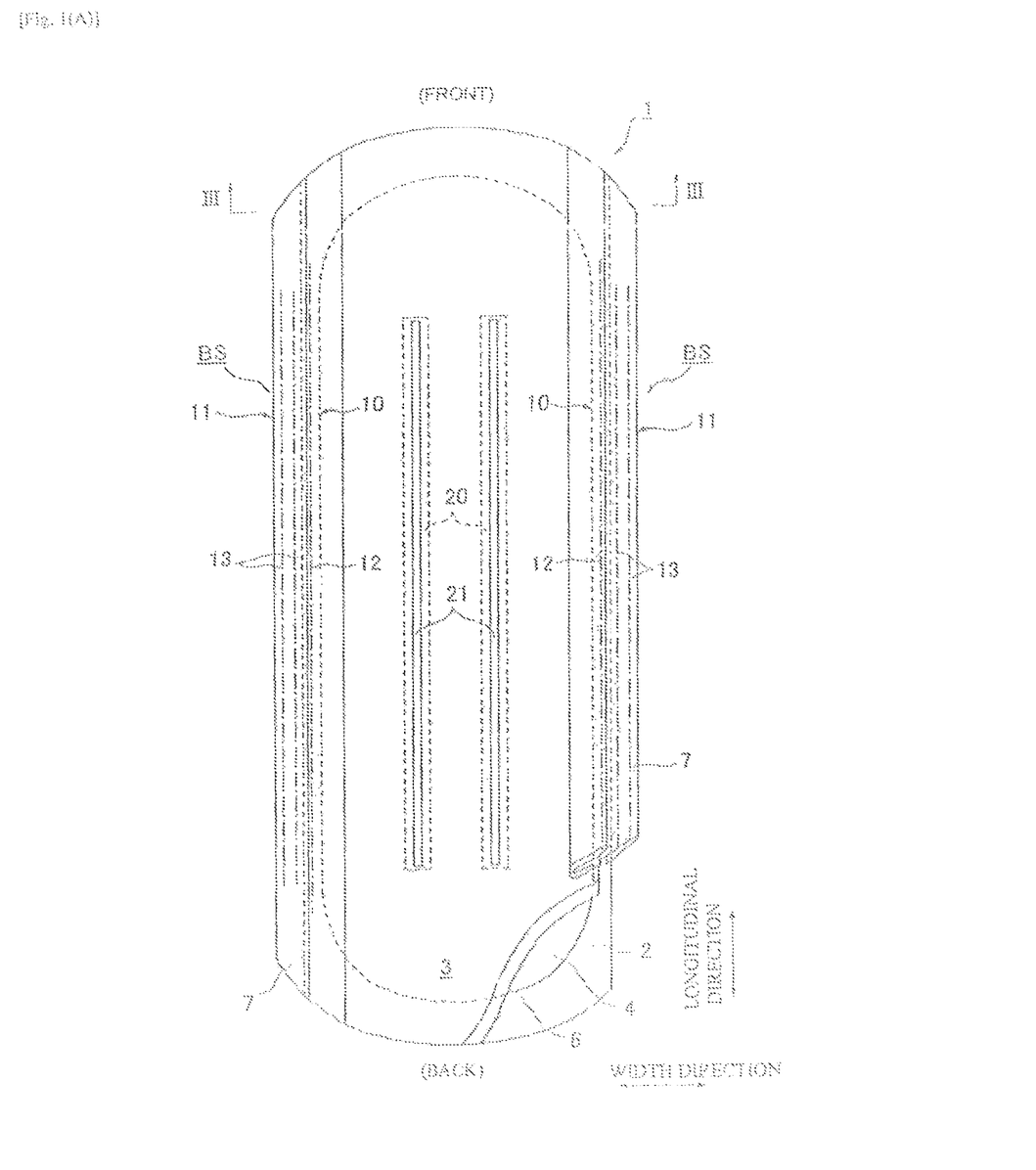
FIG. 1(A) is a partially broken development view of an incontinence pad of the invention slightly different from the incontinence pad of FIG. 1.

The above-described embossed part 21 is imparted from a front surface of the permeable front surface sheet 3, with at least the permeable front surface sheet 3 and the absorber 4 in a stacked state, by means of an emboss having a maximum width smaller than a groove width of the absorber recessed part 20. The embossing to form the embossed part 21, causes the edges of the mouth of the recessed part 20 at a skin side surface of the absorber 4, to become rounded and to form the recessed past into a sectional shape having inclined side sufaces which converge in a direction toward the bottom surface of the groove so that the groove width becomes narrower as it goes from a front surface to a non-skin side. Thus, even when an external force is applied and the groove width becomes slightly narrower, the recessed groove does not completely disappear but gradually becomes narrower toward the bottom surface. Therefore, although the absorption performance of body fluid is slightly degraded, a certain degree of the absorption performance is maintained. The only difference between the incontinence pads of FIG. 1 and FIG. 1(A) is that the latter has two parallel absorber recessed parts 20 and corresponding embossed parts 21.

When the second sheet 6 is disposed between the permeable front surface sheet 3 and the absorber 4 as in the present embodiment, the embossed part (embossment) 21 is integrally imparted to the permeable front surface sheet 3 and the second sheet 6 in a stacked state. Further, when the absorber 4 is surrounded by a covering sheet, the covering sheet is also embossed together with the permeable front surface sheet 3 as well as the second sheet, if any.

The embossed part 21 is formed with a dimension smaller in a pad width direction than the absorber recessed part 20. While the width of the embossed past 21 is not greater than the width of the bottom surface of the recessed part 20, the embossed part may extend lengthwise beyond the recessed part. The embossed part 21 may be formed in a bottom part of the absorber recessed past 20 by simply applying pressure without heat sealing, or by thermal fusion bonding or ultrasonic fusion bonding the permeable front surface sheet 3 with the second sheet 6 and synthetic fibers of the absorber 4, i.e., bonding together the permeable front surface sheet 3, the second sheet 6 and the absorber 4.

Figure 6A:
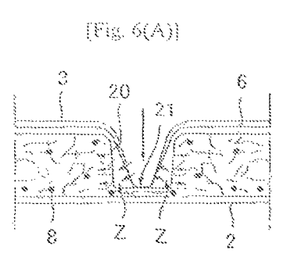
FIG. 6(A) is a sectional view showing the absorber being permeated with body fluid.

Thus, since the emboss width A of the embossed part 21 is formed smaller than the groove width B of the absorber recessed part 20, as shown in FIG. 6(A), when body fluid that flows on a surface of the permeable from surface sheet 3 flows into the embossed part 21, the body fluid goes through the permeable front surface sheet 3 and the second sheet 6 and is temporarily stored in a buffer zone Z formed between a side surface of the absorber recessed part 20 and the permeable front surface sheet 3. After that, the body fluid diffuses along the absorber recessed part 20 in a front-back direction and is absorbed and held in the absorber 4 via a side surface of the absorber recessed part 20. Therefore, even when a large amount of urine is discharged at once, the urine can be rapidly absorbed by temporarily storing in the buffer zone Z.

Figure 6B:
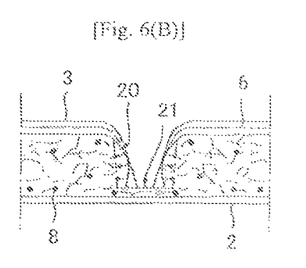
FIG. 6(B) is a sectional view showing the absorber expanding during liquid absorption.

Further, because the absorber recessed part 20 is formed without relying on compression, when body fluid permeates inside the absorber recessed part 20, the polymer 8 or pulp surrounding the absorber recessed part 20 is swollen by absorbing body fluid as shown in FIG. 6(B). Moreover, in comparison with a pad in which a high density region of the pulp or polymer is formed on the bottom part by compression, the embossing on the bottom surface of the groove in the present invention is very small. Further, even when both side surfaces of the absorber recessed part 20 bulge inward, the bulging is limited by the permeable front surface sheet 3 interposed in the absorber recessed part 20 and anchored by the embossed part 21. Therefore, clogging of the absorber recessed part 20 by the polymer 8 or pulp expanded during water absorption to deteriorate the absorption property of body fluid is prevented.

Further, since the absorber recessed part 20 is formed by fiber stacking or by a fiber stacking structure of the absorber 4a, 4b, without relying on compressions and, therefore, without consolidation by compression or hardening due to heating/melting of the absorber, flexibility intrinsic to the absorber can be maintained and excellent wearability can be maintained.

Further, due to the embossing from a front surface of the permeable front surface sheet 3, the embossed part 21 is disposed in the inside of the absorber recessed part 20. Therefore, the permeable front surface sheet 3 is interposed in the inside of the absorber recessed part 20, and a structure in which the absorber recessed part 20 hardly constricts and can rapidly absorb body fluid even when external force is applied can be maintained.

The emboss width A of the embossed part 21 is, as shown in FIG. 4, formed smaller than the groove width B of the absorber recessed part 20 (A<B), and a ratio of the emboss width A of the embossed part 21 and the groove width B of the absorber recessed part 20. A/B, is set to 0.5 or more and less than 1, preferably to 0.6 or more and less than 0.83. Thereby, between a side surface of the absorber recessed part 20 and the permeable front surface sheet 3 (second sheet 6), buffer zones Z, Z that temporarily store the permeated body fluid and become a buffer region when the superabsorbent polymer 8 or pulp absorbs water and swells are appropriately formed. It should be noted that when the absorber recessed past 20 is formed into a recessed groove shape, both side surfaces may be formed into a slope shape of a defined angle. At this time, the groove width B of the absorber recessed part 20 is made to take a width of a bottom past (formed by the impermeable back surface sheet 2) of the absorber recessed part 20.

Figure 7:
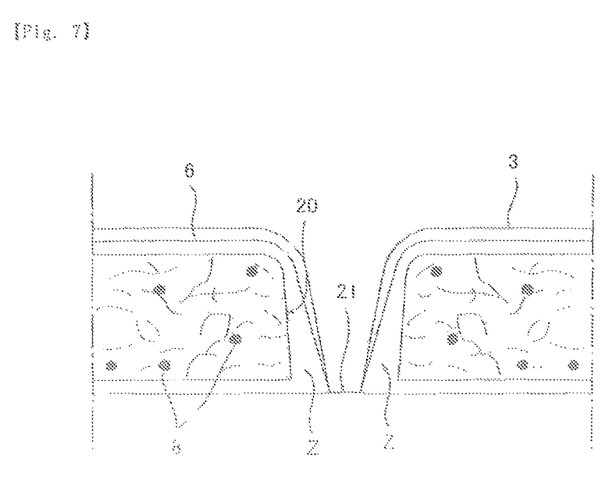
FIG. 7 is an enlarged sectional view of the vicinity of the absorber recessed part 20 according to another embodiment.

The absorber recessed part 20 may be formed without passing completely through the absorber 4, in which the absorber 4 is present at the bottom part as shown in FIG. 4 or may completely pass through the absorber 4 so there is a passage from a skin side to a non-skin side of the absorber 4 without absorbing material as shown in FIG. 7 (i.e., slit shape). When formed into a slit shape, the embossed past 21 is imparted from a front surface of the permeable front surface sheet 3 to the impermeable back surface sheet 2. It should be noted that the absorber recessed part 20 is preferably formed without completely passing through the absorber because receiving of the embossing by absorber material makes the embossing firmer, and the absorber recessed past 20 becomes stronger in terms of stiffness and constricts less when the absorber absorbs body fluid than one passing entirely through the absorber.

Figure 8A:
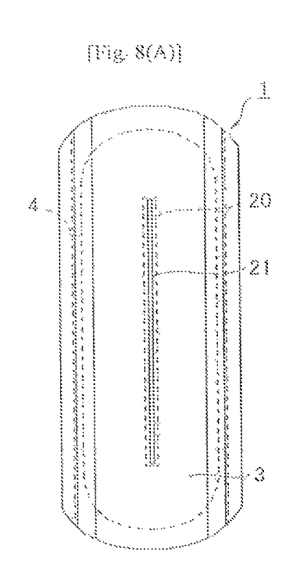
FIG. 8(A) and FIG. 8(B) show plan views of the incontinence pad 1.
Figure 8B:
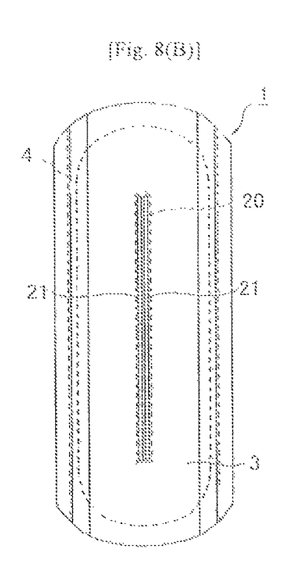

As a planar arrangement of the embossed part 21 to the absorber recessed part 20, either one embossed part 21 is disposed at a center in a width direction within the absorber recessed part 20 as shown in FIG. 8(A), or one embossed part 21 can be disposed on each of both sides within the absorber recessed past 20 as shown in FIG. 8(B). In the latter case, it can be prevented that an unnecessary part of the absorber recessed part 20 is compressed and the recessed part 20 become hard due to the embossed pasts 21, 21 suppressing bulging of the left and right parts within the absorber recessed part 20.

On the other hand, as the absorber recessed part 20, only one section may be formed at a center part in a pad width direction with respect to the absorber 4 as shown in FIG. 1 or a plurality of sections may be formed along a longitudinal direction spaced in a width direction (see FIG. 14). It should be noted that when a plurality of sections of the absorber recessed parts 20 are provided, the embossed part 21 is imparted to each of the absorber recessed parts 20.

A dimension of the absorber recessed part 20 is preferably set so that a length in a pad longitudinal direction is 100 to 180 mm, and the groove width B is 5 to 30 mm. Further, a dimension of the embossed part 21 is preferably set so that a length in a pad longitudinal direction is 90 to 170 mm and the emboss width A is 3 to 25 mm. The dimensions of the embossed past 21 are smaller than the dimensions of the absorber recessed part 20, and for operational convenience on forming the embossed past 21, it is preferred that the longitudinal dimension of the embossed part 21 be smaller than the length of the recessed part 20 by about 20 mm and the emboss width be smaller than the groove width by about 5 mm.

Figure 9A:
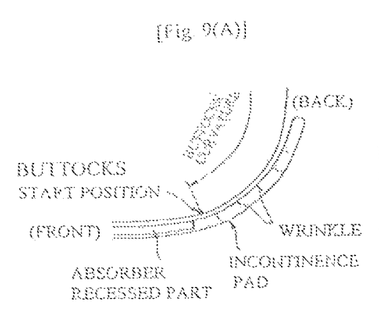

A position of a back-end part of the absorber recessed part 20 will be described with reference to FIG. 9. On a back side of a buttocks start position on a crotch side of the wearer (roughly a back side of the crotch part of underwear), because the incontinence pad 1 curves along the buttocks with respect to a longitudinal front-back direction direction, a plurality of widthwise wrinkles are formed on a pad front (i.e., skin facing) surface accompanying the curvature. Here, as shown in FIG. 9(A), when a back-end of the absorber recessed part is hypothetically no further rearward than about the start position on the crotch side of a wearer, when body fluid is discharged from a body fluid discharging site, lateral leakage of the body fluid tends to occur because the body fluid moves in a width direction via the wrinkles which are rearward of the back-end of the absorber recessed part and does not reach the absorber recessed part.

Figure 9B:
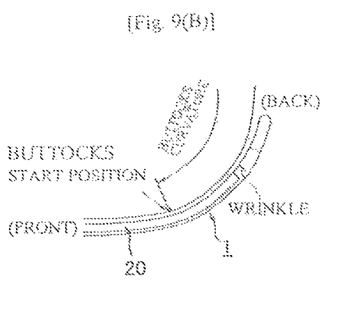
Figure 9C:
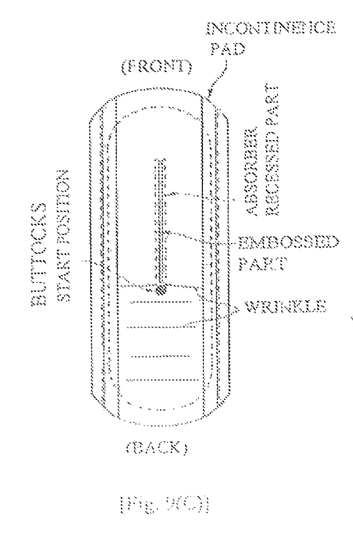
Figure 9D:
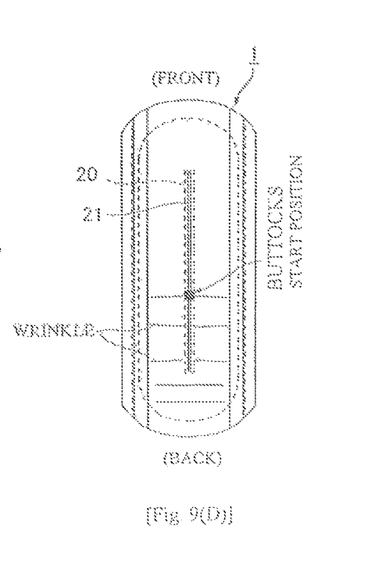

Therefore, as shown in FIG. 9(B), the back-end of the absorber recessed part 20 is preferably disposed so as to extend rearwardly to a back side (a back side of a crotch part of underwear) substantially beyond the buttocks start position on a crotch side of the wearer so that a substantial proportion of the wrinkles communicate with the absorber recessed part and, therefore, body fluid does not leak laterally. (Of course, the representations of wrinkles in the drawings is only schematic and, in practice, many closely spaced wrinkles would be present.) Because the absorber of the absorber recessed part 20 is thin, even when the pad is curved along the roundness of the buttocks, wrinkles are not formed in a pad width direction in the absorber recessed part 20, and the absorber recessed part 20 extends smoothly to the back-end part without being wrinkled, so that body fluid surely flows through the absorber recessed part 20 to be absorbed by the absorber 4 so that lateral leakage and back leakage do not occur.

Figure 10A:
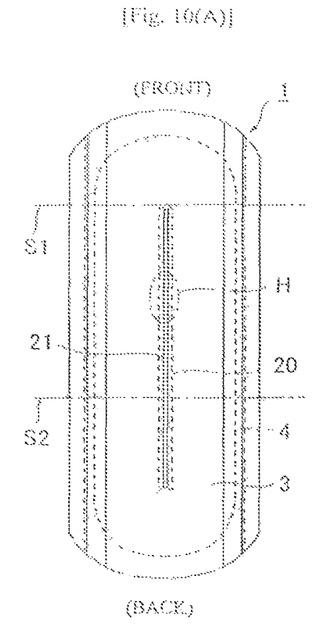
FIG. 10(A) and FIG. 10(B) are plan views of the incontinence pad 1 showing a three-fold configuration and a four-fold configuration, respectively.
Figure 10B:
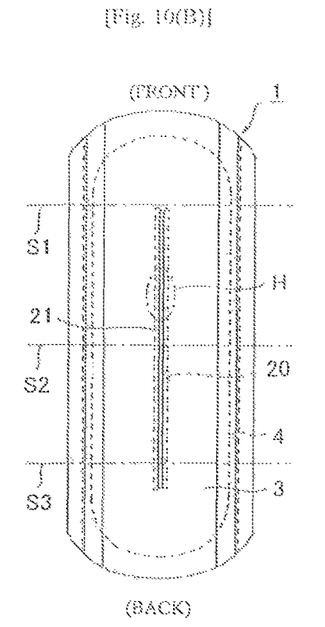

The back-end position of the absorber recessed part 20 may be determined by the relationship with one or more widthwise folding lines when the incontinence pad 1 is individually packaged, as shown in FIGS. 10(A), 10(B). For example, the back-end of the absorber recessed part 20 is preferably disposed so as to extend further to the back than a widthwise folding line S2 positioned behind the body fluid discharge site H. Thus, as was described above, the back-end of the absorber recessed part 20 can be positioned substantially further on the back side than the buttocks start position on the crotch side of the wearer. FIG. 10(A) shows a case where the incontinence pad 1 is folded up respectively into three along widthwise fold lines S1 and S2, and FIG. 10(B) shows a case where the incontinence pad 1 is folded up into four along widthwise fold lines S1 to S3.

Figure 11:
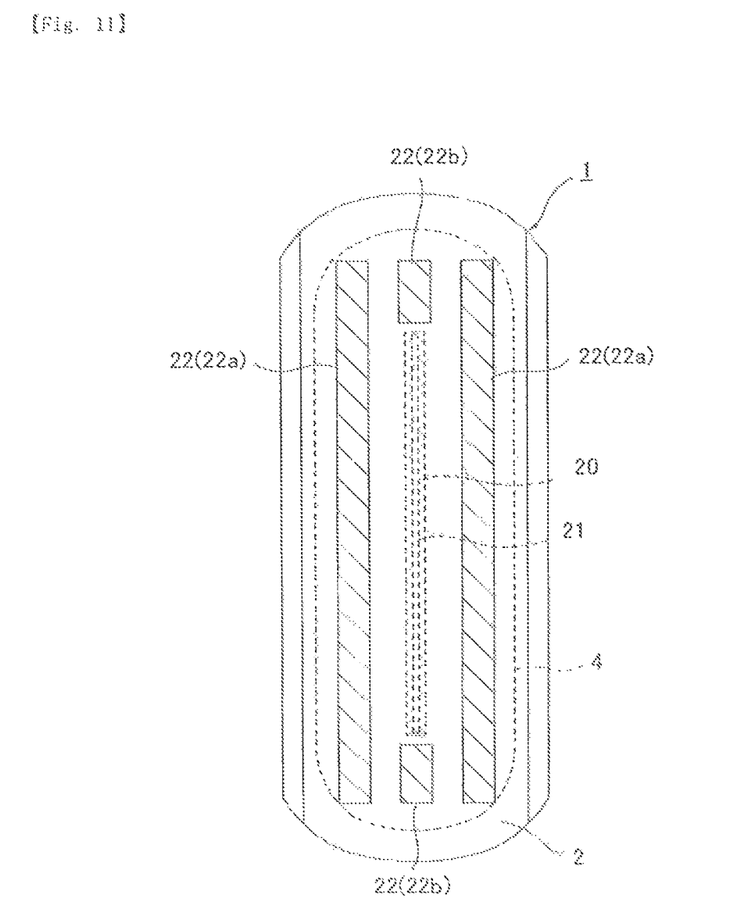
FIG. 11 is a back surface view of the incontinence pad 1.

In the present Incontinence pad 1, as shown in FIG. 11, on an external surface of the impermeable back surface sheet 2, a plurality of sections of slippage prevention adhesive layers 22, 22 . . . are formed by an appropriate coating pattern for fixing to underwear. In the present incontinence pad 1, it is preferable that the slippage prevention adhesive layer 22 is not disposed in a region that overlaps with the absorber recessed part 20. Although the region where the absorber recessed part 20 is formed is a region in which deformation tends to occur because the absorber is thin and low in rigidity, i.e., pliable, if the slippage prevention adhesive layer is disposed in a region that overlaps with such a region, there is a risk that the absorber recessed past 20 will deform as the underwear moves and a recessed groove shape may not be maintained. Further, it is likely that, when a kink in underwear occurs, the slippage prevention adhesive layers will adhere with each other to generate a kink in the product which will prevent the absorber recessed part from functioning. Therefore, when the slippage prevention adhesive layer 22 is not disposed in a region that overlaps with the absorber recessed part 20, the recessed groove shape of the absorber recessed part 20 can be maintained, the product is prevented from generating kinks, and body fluid can be surely absorbed. When only one section of the absorber recessed part 20 is disposed along a longitudinal direction at a center in the width direction of the incontinence pad 1, preferably, on each of both sides of the absorber recessed part 20, one section or a plurality of sections (one section in the illustrated example) of the slippage prevention adhesive layers 22a, 22a is disposed over almost the entire length in a pad longitudinal direction longer backward and forward than the absorber recessed part 20, and the slippage prevention adhesive layers 22b, 22b that go along the pad longitudinal direction are preferably disposed backward and forward from a position that is a center part in the pad width direction and spaced in the pad longitudinal direction from front and back end parts of the absorber recessed part 20.

Figure 12:
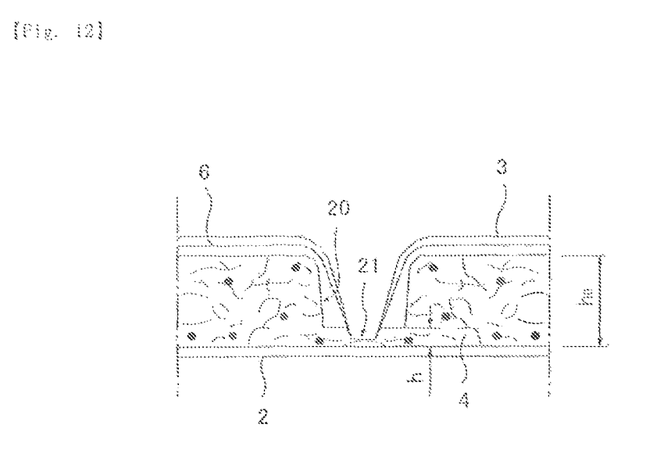
FIG. 12 is an enlarged sectional view of the vicinity of the absorber recessed part 20 according to another embodiment.

EXAMPLES OF OTHER EMBODIMENT (1) In the above example of an embodiment, when the absorber recessed part 20 is formed into a bottomed recessed groove shape, the embossed part 21 was imparted by embossing to a depth substantially the same as that of the surface of the bottom of the absorber recessed part 20, i.e., embossed without significantly compressing the absorber. However, as shown in FIG. 12, the embossing of the surface of the bottom of the absorber recessed part 20 may also be more heavily imparted to a predetermined depth so as to substantially compress the absorber. Thus, since the rigidity of the absorber recessed past 20 is thereby increased, deformation becomes difficult to occur, and a volume of space in the absorber recessed part 20 is increased, whereby an amount of body fluid that can be temporarily stored increases, and the functionality of the absorber recessed part is further improved. Further, although the superabsorbent polymer or the like expands during water absorption, the expansion into the absorber recessed part 20 is limited because the absorber recessed part 20 is formed in advance without relying on compression. Further, since a the recessed part is compressed only limitedly by the embossing 21, it hardly expands compared with a case of not compressing.

It should be noted that a height h (thickness) of a bottom part of the absorber recessed part 20 (i.e., the part of the absorber below the lowest level of the emboss) is preferably 50% or less of a height $h_0$ of the balance of the absorber 4 as shown in the same FIG. 12. Further, a basis weight of the bottom part of the absorber recessed part 20 is preferably 0 to 200 mg/m² (0 being for such configuration as shown in FIG. 7).

Figure 13A:
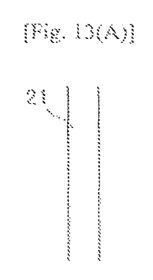
FIGS. 13(A) to (D) each show an embossed pattern of an embossed part 21.
Figures 13B, 13C:
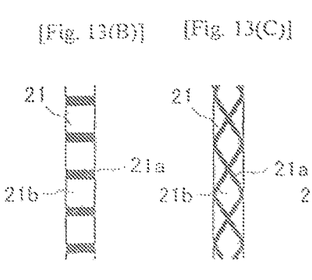
Figure 13D:
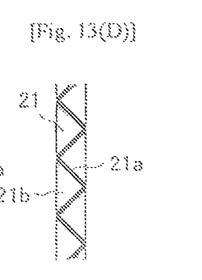

(2) An emboss pattern of the embossed part 21 can be arbitrarily selected. As shown in FIGS. 13(A), (B), (C), (D), it can be an emboss pattern formed with a pattern of flat grooves as in FIG. 13(A), or emboss patterns formed with a pattern obtained by combining high compression parts 21a and low compression pasts 21b as in FIGS. 13(B), (C) and (D). However, in order to increase the stiffness of the absorber recessed part 20 and to prevent the absorber recessed part 20 from collapsing, it is preferable to form the embossing with high compression parts 21a and low compression parts 21b. Among these, as shown in FIGS. 13(C) and (D), an emboss pattern in which the high compression parts 21a criss-cross or form triangles are particularly excellent from the viewpoint of increasing rigidity to an external force.

The invention claimed is:

1. An absorbent article comprising an absorber interposed between a permeable front surface sheet and a back surface sheet,
   wherein the absorber includes an uncompressed absorber recessed part of a groove shape into which the permeable front surface sheet is received, the groove extending lengthwise of the absorbent article over a predetermined range of the absorbent article, the groove being midway a width of the absorbent article and the predetermined range including a body fluid discharge site of a wearer of the absorbent article,
   wherein, at least one embossed part is provided having an emboss embossed onto a front surface of the permeable front surface sheet at a bottom of the groove in an area centered with respect to width of the groove and extending along the groove in a lengthwise direction of the groove, and the embossing affixing the permeable front surface sheet to the back surface sheet at the bottom of the groove only at said area, and the emboss being of width A smaller than width B of the groove,
   wherein a ratio A/B is 0.6 or greater and less than 0.83 thereby forming within the groove respective empty buffer zones between respective longitudinal side walls of the groove and those areas of the permeable front surface sheet which are received in the groove but not affixed to the bottom of the groove, whereby the buffer zones are configured to temporarily store body fluid which has passed through the permeable front sheet and not yet been absorbed by the absorber.

2. The absorbent article according to claim 1, comprising an additional sheet disposed between the permeable front surface sheet and the absorber, and wherein the additional sheet is received in the groove together with the permeable front surface sheet and is affixed to the bottom of the groove by the emboss together with the permeable front surface sheet.

3. The absorbent article according to claim 1, wherein a back end of the absorber recessed part is arranged to extend rearwardly beyond the crotch of underwear when the absorbent article is worn inside the underwear.

4. The absorbent article according to claim 1, wherein a slippage prevention adhesive layer is disposed on an external surface of the back surface sheet so as to adhere to a wearer's panties or underpants, and the slippage prevention adhesive layer does not overlap the absorber recessed part.

* * * * *